United States Patent [19]
Wack et al.

[11] 4,369,252
[45] Jan. 18, 1983

[54] FERMENTATION PROCESS FOR THE PREPARATION OF ERGOT ALKALOIDS, PRIMARILY ERGOCORNINE AND β-ERGOCRYPTINE

[75] Inventors: Géza Wack; János Kiss; Zsuzsa Lengyel née Szemenyei; Lajos Nagy; Eva Udvardy Nagy née Cserey Pechány; Karoly Zalai; Erzsebet Zsoka née Somkuti, all of Budapest, Hungary

[73] Assignee: Richter Gedeon Vegyeszeti Gyar Rt., Budapest, Hungary

[21] Appl. No.: 232,172

[22] Filed: Feb. 6, 1981

[30] Foreign Application Priority Data

Feb. 8, 1980 [HU] Hungary .................................... 282

[51] Int. Cl.[3] ........................ C12P 17/18; C12N 1/14; C12R 1/645

[52] U.S. Cl. .................................... 435/119; 435/254; 435/911

[58] Field of Search ................................ 435/119, 254

[56] References Cited

U.S. PATENT DOCUMENTS 3,884,762 5/1975 Wack et al. ........................ 435/119

*Primary Examiner*—Alvin E. Tanenholtz
*Attorney, Agent, or Firm*—Karl F. Ross

[57] ABSTRACT

The invention relates to a new process for the preparation of ergot alkaloids, primarily ergocornine and β-ergocryptine, by subjecting a Claviceps purpurea strain to fermentation under aerobic conditions in a culture medium which contains carbon and nitrogen sources, mineral salts and optionally other additives, too. According to the invention a Claviceps purpurea variant strain deposited under No. MNG 00186 is applied as alkaloid-producing strain.

4 Claims, No Drawings

FERMENTATION PROCESS FOR THE PREPARATION OF ERGOT ALKALOIDS, PRIMARILY ERGOCORNINE AND β-ERGOCRYPTINE

The invention relates to a new fermentation process for the preparation of ergot alkaloids, primarily ergocornine and β-ergocryptine, by applying a new Claviceps purpurea strain.

It is known that the pharmaceutically active component of the drug dihydroergotoxine, prepared by the hydrogenation of ergotoxine, is a mixture of dihydroergocristine, dihydroergocornine and dihydroergocryptine (Hungarian Pat. No. 129,061). It is also known that ergocryptine exists in two forms [W. Schliern et al.: Experientia 23, 991 (1967)]: in addition to α-ergocryptine, the previously identified form, β-ergocryptine can also be isolated from ergot plants. The characteristic biological effects of β-ergocryptine, isolated by plant extraction or prepared in a semisynthetic way, are as follows: adrenolytic activity, serotonine antagonism, uterus motility, influencing of the vasocular tone.

The first Claviceps purpurea strain which produces primarily β-ergocryptine was described in the Belgian Pat. No. 824,987. This strain was designated as FI-7374 in the strain collection of the firm Farmitalia.

When propagating this strain under aeration at 24° C. in a culture medium which contains e.g. sucrose, glucose or mannitol as carbon source and e.g. asparagine, peptones, hydrolyzed caseine and ammonium salts as a nitrogen source, a total alkaloid concentration of 950 to 1240 γ/ml can be attained within 10–16 days. The resulting mixture of alkaloids contains β-ergocryptine and accompanying alkaloids in a ratio of 7:3, and the latter fraction is characteristically rich in ergosine. Thus the metabolism product of the above strain cannot be used directly, i.e. without separating the ergosine component, for the preparation of ergotoxine.

In our research work feral Claviceps sclerotium, collected on a rye field not infected artificially, was used as the starting substance, and the fungus strain cultivated therefrom was subjected to repeated selection as described in the Hungarian patent specification No. 151,724, by alternately isolating the colonies and subjecting them to enrichment in a liquid culture medium. In this way a stable strain was obtained, which proved to be a new variant of Claviceps purpurea.

Selection is based on the fact that the alkaloid-producing strain forms colored colonies on the solid culture medium described in the above Hungarian patent specification, which can be easily distinguished from the white colonies of the strains which do not produce alkaloid.

The colonies of the alkaloid-producing new strain are isolated and inoculated onto a so-called differentiating culture medium for enrichment. This differentiating culture medium contains sucrose, succinic acid and glycine as major components, in addition to mineral salts and inorganic phosphate salts.

Isolation and enrichment are repeated several times to obtain the new variant strain with the following main characteristics: the growth of the culture is slow by comparison to wild Claviceps cultures, the strain does not form conidia and has a yeast-like microscopic morphology in each of the media examined, i.e. thread-like hyphae characteristic of micelial form are absent. The strain was designated as CLY strain in our laboratory.

Macroscopic characteristics of the strain:

(1) Colonies appearing on indicating starch—tryptophane—agar medium:

At 10 days age: orange-pink coloured, sharp-edged colonies with wrinkled surfaces, 6–8 mm in diameter.

At 20 days age: radially wrinkled, centrally tapering violet-pink colored colonies, 20–25 mm in diameter. The reverse is dark brown, the color of the culture medium surrounding the colonies turns violet.

(2) Colonies appearing on malt-agar culture medium:

At 10 days age: regular hemisphere-formed, light beige colored colonies, 1–2 mm in diameter.

At 20 days age: the growth is weak, the colonies darken to a brownish shade, their diameter is 2–4 mm.

(3) Colonies appearing on St agar culture medium:

At 10 days age: sharp-edged, centrally tapered colonies with diagonal wrinkles toward the center, 8–12 mm in diameter. The height of the peak is 3–5 mm. The colonies are beige—light brown colored.

At 20 days age: light brown, cocoa shaded colonies with crater-like, protruding peaks. The surface is strongly wrinkled, and the wrinkles branch off to the edges. The diameter of the colonies varies between 25 and 40 mm, their height is 6–8 mm. The colonies are difficult to separate from the agar surface. No spore formation can be observed.

Microscopic appearance of the strain in liquid cultures 40 hours culture in GK medium: Mainly single cells or colonies composed of a few number of cells appear. The cells are of cylindrical, rounded or irregular shape, 4–8×8–20μ, frequently with terminal and lateral cleavages. The cell rows are short, composed of a few number of cells. When examined under phase-contrast microscope, the cells are strongly granular and the older cells contain vacuoli. No spore formation can be observed.

40 hours culture in St medium: The microscopic appearance is essentially the same as described above, with the difference that on this culture medium colony or cell row formation is more frequent, the dimensions of the individual cells are shifted to the upper values, and no vacuoli appear in older cells, either.

The compositions of the St, St-agar and GK culture media applied in the above examinations are described in detail in the Examples.

The starch-tryptophane-agar (St-agar) medium has the following composition:

| | |
|---|---|
| starch | 20 g |
| tryptophane | 1 g |
| potassium chloride | 1 g |
| diammonium hydrogen phosphate | 2 g |

The pH of the solution of the above components is adjusted to 6.6 to 6.8, the liquid is diluted with water to 1000 ml, and then 25 g of powdered agar (Difco) are added. The resulting mixture is boiled, distributed to bottles in portions of 150 ml, and then sterilized.

The melt-agar medium has the following composition:

| | |
|---|---|
| malt extract | 60 g |
| water | to 1000 ml |
| powdered agar (Difco) | 25 g |

The culture medium is boiled, distributed to bottles in portions of 150 ml, and then sterilized.

Biochemical characteristics of the strain

The strain decomposes sucrose with β-fructofuranoside enzyme with formation of transfer oligosaccharides. The strain utilizes citric acid well. The strain produces anthraquinone-type pigments, primarily hydroxyanthraquinones.

This strain produces alkaloids upon cultivation on known culture media containing sugar and ammonium salts of organic acids. The alkaloid mixture contains 25–30% of β-ergocryptine, the bulk (55–60%) of the alkaloid mixture is ergocornine, whereas the balance is α-ergocryptine. In addition to the characteristic peptide alkaloids the strain produces ergometrine only.

The above new Claviceps purpurea variant strain was deposited at the Hungarian National Collection of Strains on 9th May, 1979 under No. 00186 MNG.

Uon examining the practical utility of the new Claviceps purpurea MNG 00186 strain it was found that the strain is capable of producing certain components of ergotoxine, i.e. ergocornine, α-ergocryptine and β-ergocryptine, by fermenting it under aerobic conditions in a culture medium containing carbon and nitrogen sources, mineral salts and optionally other additives, too.

It has also been found that when the new variant strain is utilized for alkaloid production and valine and/or isoleucine is added to the fermentation broth as precursor for the compounds to be formed, the amount of alkaloids produced in the fermentation broth increases.

Based on the above, the invention relates to a new microbiologic process for the preparation of ergot alkaloids, primarily ergocornine and β-ergocryptine, by culturing a Claviceps purpurea strain under aerobic conditions in a culture medium containing carbon and nitrogen sources, mineral salts and optionally other additives, too. According to the invention a Claviceps purpurea variant strain deposited under No. MNG 00186 is used as the alkaloid-producing strain.

Fermentation is performed according to the invention in a submerged culture under aerobic conditions, utilizing a liquid culture broth which contains carbon and nitrogen sources, mineral salts and optionally other additives as well.

Fermentation is performed at 20° to 26° C. for 4 to 8 days; the pH of the culture medium is maintained between 5.2 and 6.8.

If desired, an additive which increases the amount of the alkaloids produced (i.e. a precursor), such as valine and/or isoleucine, is also added to the fermentation broth.

The precursor is used in an amount of 0.05–5 g/100 ml, preferably 0.1–0.3 g/100 ml of fermentation broth. The precursor is used as an aqueous or slightly acidic aqueous solution, which is introduced into the fermentation broth after sterilization. The solution can be added either at once or in portions; alternatively the solution can be introduced continuously during a certain period of the fermentation.

The total alkaloid content of the fermentation broth was determined by photometry on the basis of color reactions. We do not consider this value as a specific characteristic of the process, although previous patents frequently characterize the production level in terms of the total alkaloid content determined by spectrophotometry.

To characterize the fermentation process, the individual ergotoxine components were determined separately by elution chromatography or quantitative liquid chromatography.

The main advantages arising from the use of the new strain in comparison with the known methods are as follows:

(1) Compared to plant extraction methods, fermentation represents a more developed technical solution, since it is free of the disadvantages of the agricultural background and can be controlled from charge to charge by direct technical interventions.

(2) In the fermentation process the complicated molecule can be built up from simple industrial raw materials (sucrose, ammonia) at 24° C. utilizing only air and the living cell, whereas the semisynthetic method consists of numerous sophisticated reaction steps. Moreover, in the known semisynthetic methods only the peptide chain of the molecule is built up by chemical synthesis, whereas the lysergic acid moiety is prepared by fermentation.

(3) The strain produces practically only ergotoxine components. The small amount of ergometrine produced, which is a water-soluble substance, can be removed easily from the peptide alkaloids usable in the production of ergotoxine.

The invention is elucidated in detail by the aid of the following non-limiting Examples.

EXAMPLE 1

A culture of Claviceps purpurea var. MNG 00186 grown on St agar medium is inoculated onto 100 ml of a GK culture medium filled into conical flasks of 500 ml capacity, and then incubated at 24° C. for 4 days on a rotary shaker (speed of rotation: 300 r.p.m.). 10 ml each of the resulting culture are used to inoculate 8 flasks containing 100 ml of St culture medium, each. The cultures are fermented at 24° C. for 7 days under shaking as described above. 2 g of valine, each, are added as precursor to 4 of the 8 flasks at the start of the fermentation. The remaining 4 flasks, to which no precursor is added, serve as controls. Fermentation is stopped on the 7th day, the control broths (e.g. the contents of the flasks without precursor) are combined, and the alkaloid content of the broth is determined. The broth contains 80 γ/ml of ergocornine, 15 γ/ml of α-ergocryptine and 30 γ/ml of β-ergocryptine.

The contents of the flasks to which precursor was added are combined as well, and the alkaloid content of the broth is determined. The broth contains 250 γ/ml of ergocornine, 25 γ/ml of α-ergocryptine and 30 γ/ml of β-ergocryptine.

The compositions of the culture media utilized in this Example are as follows:

| GK culture medium: | | |
|---|---|---|
| trypcasine | | 7.0 g |
| citric acid | | 4.1 g |
| potassium dihydrogen phosphate | | 0.3 g |
| magnesium sulfate | | 0.3 g |
| ammonium hydroxide | to reach a pH of | 5.7 to 5.8 |
| water | to | 840 ml |

84 ml or 840 ml portions of the above mixture are filled into flasks, and 16 ml or 160 ml, respectively, of a 50% aqueous glucose solution are added under sterile conditions.

| St culture medium: | | |
|---|---|---|
| sucrose | | 100.0 g |
| succinic acid | | 10.0 g |
| potassium dihydrogen phosphate | | 0.25 g |
| magnesium sulfate | | 0.25 g |
| ammonium nitrate | | 1.0 g |
| calcium chloride | | 1.0 g |
| ammonium hydroxide | to reach a pH of | 5.2 to 5.3 |
| water | to | 1000 ml |

This culture medium is sterilized either in conical flasks in portions of 100 ml each, or 100 liters of the culture medium are sterilized in a pilot plant fermenter.

St agar culture medium (Blake):

25 g of powdered agar (Difco) are added to each liter of the St culture medium with the above composition, the resulting mixture is boiled, then distributed to flasks in portions of 150 ml each and sterilized.

EXAMPLE 2

Typical 20 days old colonies of Claviceps purpurea MNG 00186 variant strain grown on St agar culture medium are separated from the agar surface, homogenized with 20 ml of sterile physiological saline, and 10 ml of the resulting suspension are used to inoculate 100 ml of a pre-sterilized St culture medium in a conic flask of 500 ml capacity. The mixture is incubated at 24° C. for 6 days on a rotary shaker, and 10 ml of the resulting culture are applied to inoculate 100 ml of a TC-54 culture medium in a conical flask of 500 ml capacity. After 3 days of shaking 10 ml of the resulting culture are inoculated onto 100 ml of a sterile St culture medium in a conic flask of 500 ml capacity. Incubation is contained for 7 days by shaking the mixture under the above conditions. The following alkaloid concentrations were determined: ergocornine: 150 $\gamma$/ml, $\alpha$-ergocryptine: 40 $\gamma$/ml, $\beta$-ergocryptine: 90 $\gamma$/ml.

The compositions of the liquid St culture medium and the St agar culture medium (Blake) are the same as given in Example 1.

The TC-54 culture medium has the following composition:

| | | |
|---|---|---|
| sucrose | | 100.0 g |
| citric acid | | 10.0 g |
| sodium chloride | | 10.0 g |
| potassium dihydrogen phosphate | | 0.5 g |
| magnesium sulfate | | 0.5 g |
| ammonium hydroxide | to reach a pH of | 5.7 to 5.8 |
| water | to | 1000.0 ml |

-continued

This culture medium is sterilized either in conical flasks in portions of 100 ml each, or 10 liters of the culture medium are sterilized in a pilot plant fermenter of 15 l capacity.

EXAMPLE 3

A 25 days old culture of Claviceps purpurea MNG 00186 variant strain grown on St agar medium (Blake) is separated from the agar surface by scraping, and homogenized with 100 ml of physiological saline. The resulting suspension is applied to inoculate 1 liter of a pre-sterilized GK culture medium in a conical flask of 3 l. capacity. The culture is shaken for 44 hours at 24° C. The resulting culture is used to inoculate 10 liters of a TC-54 culture medium in a laboratory fermenter with a total capacity of 15 liters. The mixture is fermented at 24° C. for 3 days under stirring with a speed of 240 r.p.m. and aerating at a rate of 0.25 l/l/min., and the resulting culture is used to inoculate 100 liter of a pre-sterilized St culture medium in an acid-fast laboratory fermenter with a total capacity of 150 liters.

The mixture is fermented for 6 days at 22° C. under stirring with a speed of 150 r.p.m. and aerating at a rate of 0.35 l/l/min. On the 2nd, 3rd, and 5th day of fermentation 100 g of valine, each, and 20 g of isoleucine, each, are added to the fermentation broth.

After 60 days of fermentation the broth contains 320 $\gamma$/ml of ergocornine, 60 $\gamma$/ml of $\alpha$-ergocryptine and 160 $\gamma$/ml of $\beta$-ergocryptine.

The compositions of the culture media utilized in this Example are the same as given in Examples 1 and 2.

What we claim is:

1. A microbiologic process for the preparation of the ergot alkaloids ergocornine and $\beta$-ergocryptine, which comprises fermentation culturing a Claviceps purpurea variant strain MNG 00186 under aerobic conditions in a culture medium which contains carbon and nitrogen sources and mineral salts, and recovering the ergot alkaloids.

2. The process defined in claim 1, wherein the fermentation is performed at a temperature of 20° to 26° C. and at a pH value of 5.2 to 6.8.

3. The process defined in claim 1, wherein a precursor of the alkaloids produced is added to the fermentation broth.

4. A biologically pure culture of Claviceps purpurea variant strain MNG 00186 which can be fermented to produce the ergot alkaloids ergocornine and $\beta$-ergocryptine.

* * * * *